(12) United States Patent
Bödiger et al.

(10) Patent No.: US 6,590,128 B1
(45) Date of Patent: Jul. 8, 2003

(54) INITIATION METHOD OF A METHOD FOR PRODUCING 2,2-BIS(4-HYDROXYPHENYL) PROPANE

(75) Inventors: Michael Bödiger, League City, TX (US); Rainer Neumann, Krefeld (DE); Frieder Heydenreich, Düsseldorf (DE); Michael Prein, Brasschaat (BE); Hans-Ludwig Fofonka, Willich (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/148,363

(22) PCT Filed: Nov. 17, 2000

(86) PCT No.: PCT/EP00/11465
§ 371 (c)(1),
(2), (4) Date: Sep. 5, 2002

(87) PCT Pub. No.: WO01/40155
PCT Pub. Date: Jun. 7, 2001

(30) Foreign Application Priority Data

Nov. 30, 1999 (DE) .......................... 199 57 602

(51) Int. Cl.$^7$ .............................. C07C 39/16
(52) U.S. Cl. ...................................... 568/728
(58) Field of Search .......................... 568/728

(56) References Cited

U.S. PATENT DOCUMENTS

| 3,037,052 A | 5/1962 | Bortnick ..................... 260/485 |
| 4,191,843 A | 3/1980 | Kwantes et al. ............ 568/728 |
| 5,315,042 A | * 5/1994 | Cipullo |
| 5,502,016 A | 3/1996 | Kiedik et al. ................ 502/11 |
| 5,723,691 A | 3/1998 | Cipullo et al. .............. 568/727 |

FOREIGN PATENT DOCUMENTS

| WO | 99/33777 | 7/1999 |

* cited by examiner

*Primary Examiner*—Michael L. Shippen
(74) *Attorney, Agent, or Firm*—Joseph C. Gil; Aron Preis

(57) ABSTRACT

A process for the commissioning of a process for the production of 2,2-bis(4-hydroxyphenyl)propane is disclosed. The process that entails reacting phenol with acetone in the presence of sulfonated cross-linked polystyrene resins is characterized in that the commissioning takes place with an acetone concentration reduced below, and a phenol concentration increased above, that of the optimal sustained operation state, with a reduced quantitative throughput, and in that with temperature control, the reactant quantity and the acetone content of the reactor feed are subsequently increased until the sustained operating state is reached.

4 Claims, No Drawings

INITIATION METHOD OF A METHOD FOR PRODUCING 2,2-BIS(4-HYDROXYPHENYL) PROPANE

The application relates to the commissioning of a process for the production of bisphenol.

Bisphenol production is known, and generally takes place by means of acid-catalysed reaction of phenols with carbonyl compounds. The reaction is generally carried out in fixed bed or fluidised bed reactors, and also in reactive columns.

Cross-linked sulfonated polystyrene resins (acid ion exchangers) are preferably employed as catalysts. These ion exchangers may optionally be chemically modified by co-catalysts having covalent or ionic bonds, and are macroporous or in the form of a gel U.S. Pat. No. 4,191,843; U.S. Pat. No. 3,037,052).

For efficient and economic production of, for example, 2,2-bis(4-hydroxyphenyl) propane (BPA) by reacting phenol with acetone, on the one hand the highest possible acetone conversions should be obtained at simultaneously high p,p-BPA selectivity as a result of suitable selection of the reaction conditions, and on the other hand it is crucial that the catalyst (ion exchanger) should maintain its activity over a long period in order to avoid costly catalyst replacement.

In the literature, therefore, increased attention is accorded in BPA production to the preparation and reactivation of catalysts.

Thus, EP-A 765 685 describes the way in which the previous washing and dewatering of commercial ion exchangers leads to greater product purity. EP-A 680 786 teaches that deactivated ion exchangers may be reactivated by rinsing with anhydrous phenol at fairly high temperatures.

The object is an optimised commissioning of a continuous process for the production of BPA by reacting phenol with acetone in the presence of sulfonated cross-linked polystyrene resins.

It has now surprisingly been found that the catalytic performance and service life of the catalyst system is influenced by the total quantity of reaction mixture, on the one hand, and also in addition by the composition of the reaction mixture, on the other.

The present application therefore provides a process for the commissioning of a process for the production of 2,2-bis(4-hydroxyphenyl)propane by reacting phenol with acetone in the presence of sulfonated cross-linked polystyrene resins, which is characterised in that
   a) the commissioning takes place with an acetone concentration reduced below, and a phenol concentration increased above, that of the optimal sustained operation state, with a reduced quantitative throughput, and
   b) with temperature control, the reactant quantity and the acetone content of the reactor feed are subsequently increased in step-wise or continuous manner until the sustained operating state is reached.

In principle, the condensation reaction between phenol and acetone may be carried out with an acetone concentration of up to 15 wt. %. Whereas high acetone concentrations lead to increased BPA production and consequently to increased space-time yields, the heat liberated by the condensation reaction may lead to industrial limitations. Moreover, an elevated acetone concentration leads to reduced selectivities in the reaction.

Preferably, when the reaction mixture is first contacted with the catalyst system the acetone concentration is reduced by at least 30%, preferably at least 45%, below the acetone concentration which is preferred in sustained operation. The total quantity of reaction mixture is reduced by at least 40%, preferably at least 60%, below the quantity which is preferred in sustained operation.

The intake temperatures are preferably around 45 to 80° C., particularly preferably around 50 to 65° C.

The temperature increase in the reactor is monitored by temperature measurement points on the reactor. Here, temperatures of 110° C., preferably 100° C., particularly preferably 90° C., should not be exceeded at each measurement point. The process is preferably managed such that a temperature peak travels through the reactor. When the temperature peak reaches the reactor outlet, the acetone quantity in the feed is then increased in continuous or step-wise manner up to the acetone concentration which is preferred in sustained operation. Simultaneously or preferably subsequently, the total quantity at the fixed bed reactor feed is increased in step-wise or continuous manner to the total quantity which is preferred in sustained operation. The reaction temperature is then optionally adjusted to the sustained operation temperature.

For sustained operation of BPA production phenol and acetone are utilised preferably in the ratio >5:1, particularly preferably >10:1. Here, acetone concentrations of from 2.0 wt. % to 15.0 wt. %, in particular from 3.5 wt. % to 5.5 wt. %, in the reaction mixture have proved favourable. In sustained operation the reaction generally takes place at from 45 to 110° C., preferably 50 to 80° C.

The dissolved oxygen content in the reaction mixture for commissioning and in sustained operation is preferably less than 1 ppm, particularly preferably less than 100 ppb. The dissolved or undissolved metal ion content of the reaction mixture for commissioning and in sustained operation is preferably not more than 1 ppm, particularly preferably not more than 0.5 ppm in respect of Fe, Co, Ni, Mo, Cr, Cu as individual components, and preferably not more than 10 ppm, particularly preferably not more than 1 ppm for the total of the named metals.

A stratified bed reactor or fluidised bed reactor through which the flow is upward or downward and in particular a stratified bed reactor through which flow is continuous from top to bottom is preferably employed as the reactor.

The commissioning process according to the invention is suitable for both the first start-up of a reaction system after changing the catalyst and also for recommissioning, for example following a temporary shut-down.

Commissioning with a reduced acetone concentration and an increased phenol concentration is advantageous both when pure acetone/phenol mixtures are utilised and also in the industrially preferred operation of reaction units with recycled circulating streams containing phenol, acetone, BPA, BPA isomers and by-products and as an option water.

The advantage of the procedure according to the invention resides in the avoidance of irreversible damage to the catalyst resin, as a result of controlling the acetone concentration, quantity and temperature. Such damage occurs when the catalyst system is commissioned with the acetone concentrations which are preferred in sustained operation, and is manifested as mechanical damage to the catalyst beads and coloured deposits on the surface of the catalyst beads. This damage leads to reduced catalyst activities and selectivities in sustained use and to an increased pressure build-up in sustained operation, due to a change in compressibility. Increased coloration additionally arises in the condensation reaction of phenol with acetone. The exclusion of oxygen and the control of the metal ion concentration in the reaction solution ensures that the activity of the ion exchanger is not impaired by deposits of ionic constituents and that degradation phenomena due to the effect of redox-active metal constituents and oxygen do not arise on the organic matrix of the ion exchanger. Consequently, it is possible when proceeding according to the invention to increase the BPA yield and quality in an industrially operated BPA plant, and to reduce the costly replacement of catalyst beds necessitated by deactivation.

The Examples which follow serve to explain the invention, which is not limited to the Examples.

EXAMPLE 1

Sulfonated cross-linked polystyrene resin (Lewatit SC 104, from Bayer AG) is utilised for industrial BPA production. The reaction system is operated with a dewatered mother liquor from an installation to separate crystals of BPA-phenol adduct, which is supplemented with phenol and acetone before entering the reactor. The typical composition, and that which is optimal in terms of the acetone content in sustained operation, is:

phenol: 81.0% acetone: 4.0% p,p-BPA: 9.0% isomers and higher condensates: 6.0% water: <0.1%

The throughput in sustained operation is 0.3 $m^3$ reaction solution/$m^3$ of catalyst volume*h at an intake temperature of 58° C.

Following a catalyst change the reaction system is commissioned in the following manner: the phenol-wet catalyst is transferred as a suspension in phenol (70 vol. % solids) into the reactor (adiabatically operated down-flow fixed bed reactor) at 60° C. Supernatant phenol is drawn off, and the catalyst bed is rinsed once with phenol (100 vol. %) and, after the phenol has been drawn off at the bottom, is charged up to the upper edge of the catalyst bed with phenol in counter-current. Reaction solution then impinges at 58° C. on the catalyst bed. By admixing phenol (100 wt. %) to the reaction mixture which is normal in sustained operation, a reaction mixture of the following composition is adjusted by this means:

phenol: (90.5%)

acetone: 2.0% p,p-BPA: 4.5% isomers and higher condensates: 3.0% water: <0.1%

0.06 $m^3$ reaction solution/$m^3$ catalyst volume*h (corresponding to 20% of the optimal throughput in sustained operation) flows in continuous manner through the reaction system. The temperature profile is monitored through the catalyst bed by means of temperature sensors at 20, 40, 60, 80 and 100% of the catalyst bed height. A temperature peak occurs at 85° C. which is propagated through the catalyst bed and after 15 hours is recorded at the outlet. At this time, the reaction mixture is adjusted at the reactor intake to the optimum values (4.0% acetone) for sustained operation, as indicated above. The throughput is then increased over the course of 40 hours in continuous manner from 0.06 $m^3$ reaction solution/$m^3$ catalyst volume*h to the optimal quantity for sustained operation, 0.3 $m^3$ reaction solution/$m^3$ catalyst volume*h. The adjusted values are then maintained in sustained operation.

In sustained operation over a 60-day period a catalyst commissioned in this manner demonstrates a 91% average acetone conversion and a 93.5% average selectivity for p,p-BPA formation from acetone. The average pressure build-up through the catalyst bed was 0.2 bar/m. Catalyst samples taken from the top stratum of the reactor showed an average broken catalyst bead content of 5%.

COMPARISON EXAMPLE 2

The catalyst was commissioned as in Example 1, with the exception that impingement was directly with the optimal reaction mixture (4.0% acetone) for sustained operation at a throughput of 0.1 $m^3$ reaction solution/$m^3$ catalyst volume*h, which was increased over a period of 5 h to 0.3 $m^3$ reaction solution/$m^3$ catalyst volume*h. Here, temperature peaks of 115° C. in the reactor bed were measured.

In sustained operation over a 60-day period a catalyst commissioned in this manner demonstrates an 87% average acetone conversion and a 92.2% average selectivity for p,p-BPA formation from acetone. The average pressure build-up through the catalyst bed was 0.3 bar/m. Catalyst samples taken from the top stratum of the reactor showed an average broken catalyst bead content of 15%. The catalyst beads were covered with a black surface deposit. Compared with the results from Example 1 the colour of the reaction solution at the reactor outlet was increased by an average of 5 Hazen units.

What is claimed is:

1. Process for the commissioning of a process for the production of 2,2-bis(4-hydroxyphenyl)propane by reacting phenol with acetone in the presence of sulfonated cross-linked polystyrene resins, characterised in that a) the commissioning takes place with an acetone concentration reduced below, and a phenol concentration increased above, that of the optimal sustained operation state, with a reduced quantitative throughput, and b) with temperature control, the reactant quantity and the acetone content of the reactor feed are subsequently increased in step-wise or continuous manner until the sustained operating state is reached.

2. Process according to claim 1, characterised in that on commissioning the acetone concentration is lowered by 30% or more below the optimal concentration in sustained operation.

3. Process according to claim 2, characterised in that on commissioning the quantitative throughput is reduced by 40% or more below the optimal quantitative throughput in sustained operation.

4. Process according to claim 1 characterised in that the optimal acetone concentration in sustained operation is from 2.0 to 15.0 wt. %.

* * * * *